US006300072B1

(12) United States Patent
Jensen (10) Patent No.: US 6,300,072 B1
(45) Date of Patent: Oct. 9, 2001

(54) PCR METHODS AND MATERIALS FOR DETECTING BARTONELLA SPECIES

(75) Inventor: Wayne Jensen, Wellington, CO (US)

(73) Assignee: Heska Corporation, Fort Collins, CO (US)

(*) Notice: Subject to any disclaimer, the term of this patent is extended or adjusted under 35 U.S.C. 154(b) by 0 days.

(21) Appl. No.: 09/398,179

(22) Filed: Sep. 17, 1999

Related U.S. Application Data (60) Provisional application No. 60/101,023, filed on Sep. 18, 1998.

(51) Int. Cl.[7] .............................. C12Q 1/68; C12P 19/34; C01H 21/04
(52) U.S. Cl. ............................. 435/6; 435/91.2; 435/810; 536/23.1; 536/24.32; 536/24.33
(58) Field of Search ............................... 435/6, 91.2, 810, 435/471, 252.3, 320.1; 536/24.33, 24.32, 23.1

(56) References Cited

U.S. PATENT DOCUMENTS

| 5,869,335 | 2/1999 | Munderloh et al. | 435/348 |
| 5,952,194 | 9/1999 | Stiegler | 435/69.1 |
| 5,958,414 | 9/1999 | Regnery, et al. | 424/184.1 |

OTHER PUBLICATIONS

Dauga et al. Journal of Molecular Microbiology. 45: 192–199 (No date), 1996.*
Kordick, et al., 46–3 *Int J Syst Bacteriol* 704 (1996).
Minnick & Barbian., 31 *J Microb Meth* 51 (1997).
Bass, et al., 16 *Pediatr. Infect. Dis. J.* 163 (1997).
Kordick, et al., 35(7) *J. Clin. Microb.* 1813 (1997).
Joblet, et al., 33(7) *J. Clin. Microb.* 1879 (1995).
Norman, et al., 33(7) *J. Clin. Microb.* 1797 (1995).
Birtles, 129 FEMS *Microbiol. Letters* 261 (1995).
Matar, et al., 31(7) *J. Clin. Microb.* 1730 (1993).
Roux & Raoult, 33(6) *J. Clin. Microb.* 1573 (1995).
Rikihisa, et al., 35(4) *J. Clin. Microb.* 823 (1997).
Messick, et al., 36(2) *J. Clin. Microb.* 462 (1998).
Dawson, et al., 156 *Arch Intern Med* 137 (1996).
Warner & Dawson, *Genus and Species–Level Identification of Ehrlichia Species by PCR and Sequencing*, Protocol 2 from ASM Press, Washington, D.C. (1996).
Dawston, et al., *Polymerase Chain Reaction Evidence of Ehrlichia chafeensis, an etiologic agent of human ehrlichiosis, in dogs from southeast Virginia*, 57(8) *Amer. J. Vet. Res.* 1175 (1996).
Dawson, et al., 57(1) *Am J Trop Med Hyg* 109 (1997).
Anderson, et al., 29(12) *Journal of Clinical Microbiology* 2838 (Dec. 1991).
Roux and Raoult, 156 *Gene* 107 (1995).

* cited by examiner

Primary Examiner—Carla J. Myers
(74) Attorney, Agent, or Firm—Heska Corporation (57) ABSTRACT

In broad terms, the present invention includes materials and methods useful to distinguish between and among species of a genus. The present methods utilize the differences in PCR amplicon sizes to specifically identify a given species.

15 Claims, 6 Drawing Sheets

20 bp ladder
B. bacilliformis
B. clarridgeiae
B. elizabethae
B. henselae
B. quintana
B. vinsonii (berkhoffii)
20 bp ladder

PCR METHODS AND MATERIALS FOR DETECTING BARTONELLA SPECIES

This application claims priority to U.S. Provisional Patent Application Ser. No. 60/101,023, filed Sep. 18, 1998

BACKGROUND OF THE INVENTION

The present invention is concerned with speciation of organisms, for the purpose of improving differential diagnosis of disease. The assays currently available to distinguish between or among species have not always met the expectations of consumers because they are either too costly, cumbersome or unavailable.

Polymerase chain reaction (PCR) and serological assays are currently used to distinguish among species. Serological tests present problems with cross-reactivity and available PCR tests are complicated. Typically, PCR-based assays require three steps: 1) conducting PCR using a primer set which distinguishes among members of different genera, but not among members of the same genus; 2) digesting the PCR products with restriction enzymes and 3) distinguishing among species on the basis of restriction digest patterns. One assay uses several sets of species-specific primers instead of digestion with restriction enzymes, with identification of the PCR products made by size. Minnick and Barbian, 31 *J Microb Meth* 51 (1997).

One genus of microorganisms, Bartonella, causes a variety of species-dependent disease states in humans, and is therefore important to speciate prior to treatment. Humans infected with bacteria from the genus Bartonella display a variety of pathogies, and appropriate treatment has been surmised as dependant on the species causing the pathology. For instance, the species *B. henselae* (relatively common in flea-infested areas) presents as cat scratch disease or atypical cat scratch disease, and health care professionals continue to debate the appropriate antibiotic treatment. Bass et al., 16 *Pediatr. Infect. Dis. J.*, 163 (1997). *B. clarridgeiae*, another causative agent of cat scratch disease, can be treated with antibiotics, but it is not clear which are the most appropriate. ibid.

*B. bacilliformis* is the causative agent for Carrion's disease (Oroya fever), and is typically treated with chloramphenicol, penicillins or tetracyclines. ibid. Another species, *B. elizabethae* has been associated with cardiac valve abnormalities, and is so rare that appropriate antibiotics have yet to be determined. ibid.

*B. quintana* causes trench fever (rare except for unsanitary living conditions or in the immunocompromised), and has been successfully treated with penicillins, tetracyclines and cephalosporins. Kordick et al., 35(7) *J. Clin. Microb.* 1813 (1997). *B. vinsonii sub vinsonii* and *B. vinsonii sub berkhoffii* have only been found in dogs and voles.

Available Bartonella PCR diagnostics require several steps, and are therefore inconvenient for laboratory analysis of samples. For instance, PCR assays on the basis of differences in citrate synthase sequences have been performed using a first step of conducting PCR and a second step of digesting the PCR products with restriction enzymes, followed by gel electrophoresisis to distinguish among species. Joblet et al., 33(7) *J. Clin. Microb.* 1879 (1995); Norman et al., 33(7) *J. Clin. Microb.* 1797 (1995). PCR assays on the basis of differences in 16S rRNA sequences have also been conducted, using restriction enzymes to distinguish among species. Birtles, 129 *FEMS Microbiol. Letters* 261 (1995).

Likewise, primers have been used to amplify the region between the 16S and 23S genes (called "the intergenic region") of Bartonella. In those assays, restriction enzymes were also used to cut and distinguish the PCR products. Matar et al., 31(7) *J. Clin. Microb.* 1730 (1993) and Roux and Raoult, 33(6) *J. Clin. Microb.* 1573 (1995). In Roux, a difference in size of PCR products (prior to digestion by restriction enzymes) was noted (page 1576); however, the differences are so small as to be indistinguishable on a gel. Moreover, no suggestion is made in Roux to use the pre-digestion PCR product size differences for the purpose of differentiation. In Matar, page 1732 that all three species had "an approximately 1,600-bp fragment" and bacilliformis had a 1,000 bp fragment prior to digestion.

Figure 2:
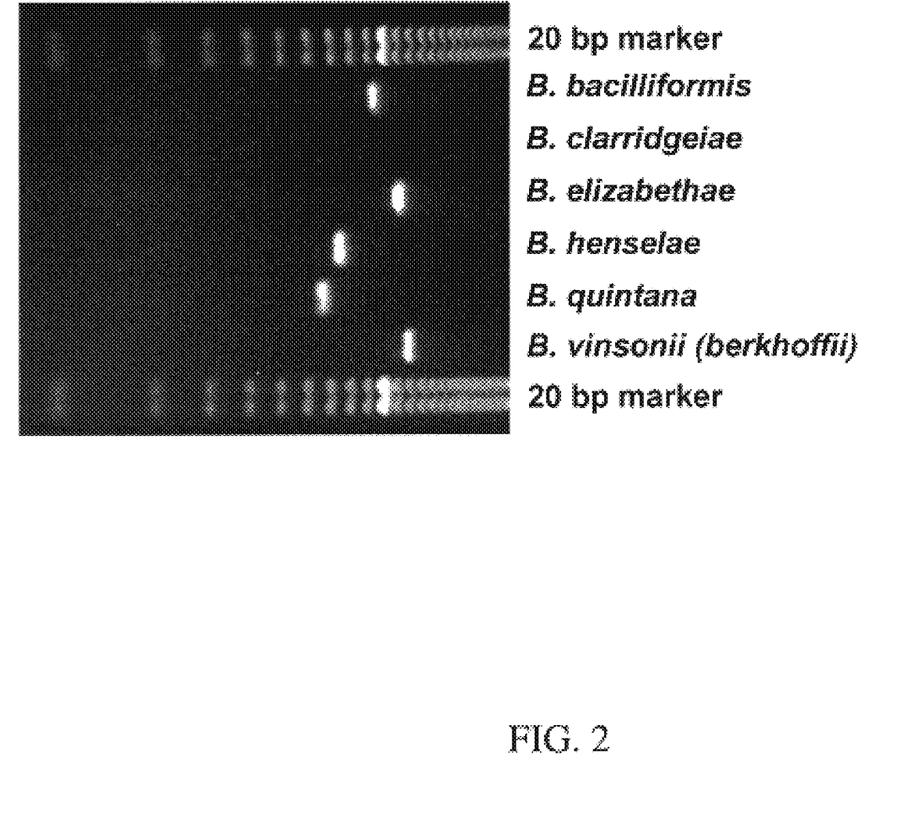
FIG. 2. PCR-based identification of Bartonella species. An ethidium bromide-stained agarose gel (3%) demonstrating amplified products from DNA template derived from Bartonella species. Bartonella bacilliformis, B. elizabethae, B. henselae, and B. quintana yielded expected products of 186 bp, 216 bp, 147 bp, and 132 bp, respectively. Template DNA from B. vinsonii (subspecies berkhoffii) yielded a PCR product of approximately 235 bp. PCR amplification of the B. clarridgeiae template DNA yielded no product. First and last lanes contain 20 base pair ladder.
Figure 3:
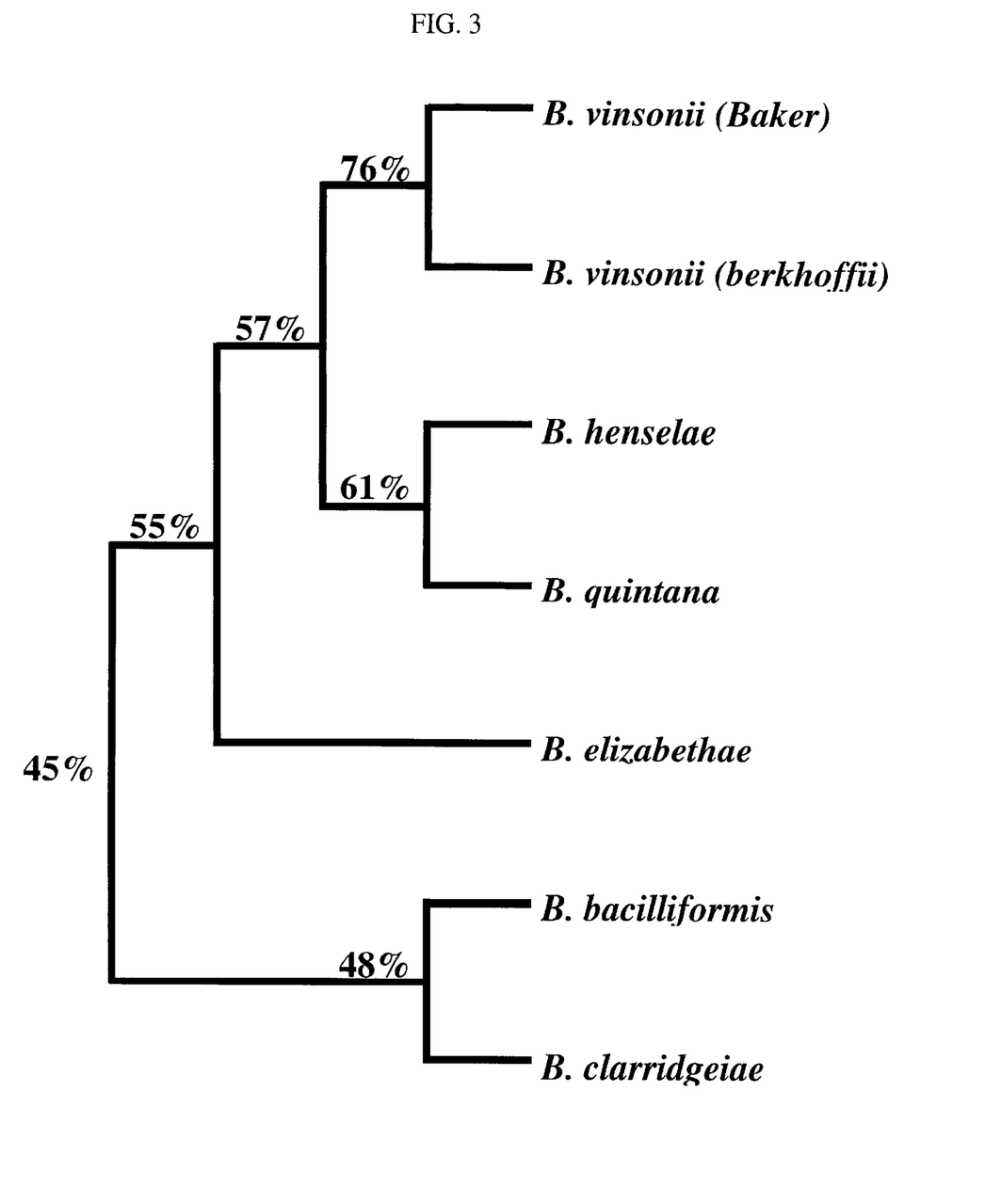
FIG. 3. Phylogenetic comparison of 16S-23S rRNA intergenic region sequences for Bartonella species. Calculated matching percentages are indicated at each branch point of the dendrogram. The lengths of horizontal and vertical lines are not significant.

In a different approach, Minnick and Barbian, 31 J Microb Meth 51 (1997) designed one set of primers from the 16S/23S intergenic region of Bartonella, and amplified fragments from *B. bacilliformis, B. elizabethae, B. henselae* and *B. vinsonii*. The fragments were of different, but indistinguishable sizes (FIG. 2), and the researchers therefore conducted a second, species-specific amplification using different sets of primers for each species represented (FIG. 3). Minnick, at 55 (1997).

Citation of the above documents is not intended as an admission that any of the foregoing is pertinent prior art. All statements as to the date or representation as to the contents of these documents is based on subjective characterization of information available to the applicant, and does not constitute any admission as to the accuracy of the dates or contents of these documents.

SUMMARY OF THE INVENTION

The present invention requires only a single step to generate amplicons which identify a specific species.

It is therefore an object to provide a simplified assay for distinguishing between or among species of a genus.

It is a specific object to provide a simplified assay for distinguishing between or among Bartonella species.

It is yet another object to provide materials (nucleic acids, vectors, cells, etc.) related to the methods disclosed, including primers and the full sequence of the 16S/23S region of two species of Bartonella.

In all of the above embodiments, it is an object to provide methods to diagnose disease using the materials and methods provided.

It is also an object to provide methods for identifying primers useful to conduct PCR assays which capitalize on the species-specific size differences in an intergenic region of a prokaryote.

It is also an object to provide methods for identifying primers useful to conduct PCR assays which capitalize on the species-specific size differences in the 16S/23S intergenic region of Bartonella.

Finally, it is an object of the invention to provide a kit for convenient use of the materials and methods herein provided.

Definitions: For the purposes of the present invention, the following terms shall have the following meanings:

"Amplicon(s)" shall mean a nucleic acid(s) produced through use of primers in PCR.

"Genus-specific primer(s)" shall mean primers capable of amplifying an amplicon from at least a portion of the 16S/23S intergenic region of at least two species of the same genus, and no other genera, and wherein the size of the amplicon is unique to the species.

"Bartonella genus-specific primer(s)" shall mean primers capable of amplifying an amplicon from at least a portion of the 16S/23S intergenic region of at least two Bartonella species, and no other genera, and wherein the size of the amplicon is unique to the species.

When the term "Genus-specific primer(s)" or "Bartonella genus-specific primer(s)" is used to describe primers used in PCR assays, it is assumed that said primers are also being in amounts sufficient to amplify at least one ascertainable fragment.

A "set" of primers means at least one forward and at least one reverse primer, that, when used in a PCR assay in appropriate amounts, is capable of amplifying an amplicon.

DETAILED DESCRIPTION OF THE INVENTION

In broad terms, the present invention includes materials and methods useful to distinguish between and among species of a genus. The methods simplify and are therefore more cost-effective than previous methods. In addition, because the present methods are simpler than previous methods, the risk of operator error, contamination, or any other technical problem is reduced, making the present invention inherently more reliable than previous methods.

The present invention includes methods to detect at least one prokaryotic species in a test sample, comprising the following steps: a.) conducting polymerase chain reaction using starting materials comprising a test sample and at least one set of genus-specific primers; and b.) detecting the prokaryotic species in the event that a species-specific sized amplicon is present. A method as described, wherein step b.) comprises gel electrophoresis is preferred, although any method for detecting amplicon(s) is within the scope of the present invention.

The present invention also includes methods to detect Bartonella species in a test sample, comprising: a.) conducting polymerase chain reaction using starting materials which comprise a test sample and at least one set of Bartonella genus-specific primers; and b.) detecting Bartonella species in the test sample in the event a Bartonella-sized amplicon is present. A method as described, wherein step b.) comprises gel electrophoresis is preferred, although any method for detecting amplicon(s), (e.g. size-differentiating chromatography) is within the scope of the present invention.

For instance, the above method can be used to identify both the specific presence, or the specific absence of a certain species of Bartonella. As an example, the present method could be used to test a sample using a primer set (for instance, one forward sequence, one reverse sequence, in amounts necessary to conduct PCR) designed to amplify, both B. bacilliformis and B. quintana, although the size of the amplicons would differ. In that instance, it is possible that the primers would amplify a fragment unique for B. quintana, and not B. bacilliformis. The result would indicate the presence of B. quintana as well as the absence of B. bacilliformis.

In another example, the present method could be used to test a sample using a primer set designed to amplify uniquely-sized amplicons from each and every known Bartonella species. Amplicons resulting from use of the genus-specific primer set would identify, by their size or absence, the species of Bartonella present and/or absent in the sample. For instance, if B. elizabethae and B. henselae-sized amplicons were present and B. quintana, B. bacilliformis and B. clarridgeiae-sized amplicons were absent, then the result would indicate the presence of B. elizabethae and B. henselae and the absence of B. quintana, B. bacilliformis and B. clarridgeiae. In fact, methods as described, wherein the primers are capable of amplifying uniquely-sized amplicons for every Bartonella species is a preferred embodiment of the present invention. However, methods wherein the primers are capable of amplifying uniquely-sized amplicons from B. henselae and B. clarridgeiae (the species which have been associated with cat scratch disease) are also preferred.

Moreover, the present invention is not limited to the use of only one set of genus-specific or Bartonella genus-specific primers. The methods herein also include those wherein a second set of primers is used, for example, for nested PCR. However, methods wherein PCR is conducted using one set of genus-specific or Bartonella genus-specific primers is preferred.

Methods which utilize primers designed using conserved sequences in or flanking the Bartonella 16S/23S intergenic region are within the scope of the present invention. The regions which span the consensus sequences in the Bartonella 16S/23S intergenic sequences from nucleotides 1–100, 130–150 and 300–350 (nucleotide numbers for *B. henselae*, Genbank Accession Number L35101) are particularly useful for designing forward primers for the present methods. A preferred region for designing forward primers for the present invention is the region spanning bases 351 through 402. Not all bases are identical in these regions, but those in the art are aware of primer design strategy in light of non-identical sequences.

The regions which span the consensus sequences in the Bartonella 16S/23S intergenic sequences from nucleotides 430–530, 860–940 and 1000–1035 (nucleotide numbers for *B. henselae*, Genbank Accession Number L35101) are particularly useful for designing reverse primers for the present methods. A preferred region for designing reverse primers for the present invention is the region spanning bases 552 through 652. Not all bases are identical in these regions, but those in the art are aware of primer design strategy in light of non-identical sequences.

Methods as above wherein the Bartonella genus-specific forward primer is selected from the group consisting of: SEQ ID NO 5; SEQ ID NO 8; SEQ ID NO 9; SEQ ID NO 11; SEQ ID NO 14; SEQ ID NO 20; and SEQ ID NO 22 are preferred. More preferred are SEQ ID NO 5; SEQ ID NO 11; SEQ ID NO 14; SEQ ID NO 20; and SEQ ID NO 22. Methods as described in the previous paragraph wherein the Bartonella genus-specific reverse primer is selected from the group consisting of: SEQ ID NO 6; SEQ ID NO 7; SEQ ID NO 10; SEQ ID NO 12; SEQ ID NO 13; SEQ ID NO 19; and SEQ ID NO 21 are preferred. SEQ ID NO 6; SEQ ID NO 10; SEQ ID NO 13; SEQ ID NO 19; and SEQ ID NO 21 are more preferred. The most preferred forward primer for use in a diagnostic assay is SEQ ID NO 20, and the most preferred reverse primer for use in a diagnostic assay is SEQ ID NO 19.

Also provided in the present invention are methods to detect Bartonella-caused disease in a mammal, comprising: a.) conducting polymerase chain reaction using starting materials which comprise a test sample and at least one set of Bartonella genus-specific primers; and b.) detecting Bartonella-caused disease in the test sample in the event a Bartonella-sized amplicon is present. A method as in this paragraph, wherein the Bartonella-caused disease is baciliary angiomatosis or cat scratch disease is preferred.

Specifically the present invention also provides methods to detect cat-scratch disease in a mammal, comprising: a.) conducting polymerase chain reaction using starting materials which comprise a test sample and at least one set of Bartonella genus-specific primers capable of amplifying *B. henselae* and/or *B. clarridgeiae* nucleic acid; and b.) detecting cat-scratch disease in the test sample in the event a *B. henselae*- and/or *B. clarridgeiae*-sized amplicon is present.

Despite the focus of the preceding paragraphs on the ability of the present invention to distinguish products from Bartonella species, the present invention is not limited thereto. The general concept of using intergenic sequences (or other variable regions) to conduct PCR so as to generate PCR products of distinguishable and distinguishing size is within the scope of the present invention. For example, the intergenic sequences, of certain Mycobacteriun species are known to be variable, and primers common to the intergenic sequences of these organisms (and which would result in size-distinguishing products) would eliminate the extra step of having to conduct restriction enzyme digests on the PCR products. Moreover, even for those organisms for which an acceptable assay exists, the present invention is useful in that it easy and convenient to conduct.

Intergenic sequences of organisms are generally available through journal publications, or through Genbank or NIH blast database. The most used database can be found at http://www.ncbi.nlm.nih.gov/. A search for intergenic sequences would typically include searching on either a known sequence or the name of the organisms to be distinguished.

The primers for the above assay can be designed using the 16S/23S intergenic sequence from *B. henselae* (Genbank accession number L35101); *B. bacilliformis* (Genbank accession number L26364); *B. quintana* (Genbank accession number L35100); *B. vinsonii sub vinsonii* (Genbank accession number L35102); *B. elizabethae* (Genbank accession number L35103) and the sequence information herein provided. Moreover, it is known in the art that primers are preferably G–C rich, ideally more than 50% of the bases being G or C. The length of the primer is usually chosen to minimize the chances of amplifying non-target nucleic acid, as well as minimize self-hybridization. Primers are typically 17 to 30 bases in length, although there are no absolute rules with regard to length or G–C content. For the purposes of the present invention, other parameters may take precedent over the length or constitution of the primers. Certain computer programs (such as MacVector) are helpful in primer design and PCR condition optimization.

The assays described herein comprise both a PCR step and an amplicon size-determination step. PCR can be conducted according to techniques known to those of skill in the art, including for example, thermocycle PCR and isothermal PCR. A number of printed publications describe these procedures. For instance Sambrook et al., *Molecular Cloning: A Laboratory Manual* (Cold Spring Harbor Laboratory Press, 1989); Ausubel et al., *Current Protocols in Molecular Biology* (Greene Publishing Associates, Inc., 1993); and Walker et al., 89 *Proc Natl Acad Sci USA* 392 (1992) describe typical parameters. Moreover, journal articles by investigators studying the organisms of interest will typically contain details about PCR amplification of the organisms' nucleic acid.

For example, thermocycle PCR can be conducted as follows: a sample is taken for amplification. Then, a thermocycler is used (at alternatingly high and low temperatures) to promote a.) dissociation of double stranded nucleic acid; and b.) hybridization of the primers to any sample nucleic acid and c.) subsequent synthesis of complementary nucleic acid. When the primers are bound to a nucleic acid in the test sample, the polymerase synthesizes a nucleic acid complementary to the sample nucleic acid, and when the primers are not bound, no synthesis takes place. A suitable biological sample includes, but is not limited to, a bodily fluid composition or a cellular composition. A bodily fluid refers to any fluid that can be collected (i.e., obtained) from an animal, examples of which include, but are not limited to, blood, serum, plasma, urine, tears, aqueous humor, cerebrospinal fluid (CSF), saliva, lymph, nasal secretions, milk and feces.

A second step in the described methods of the present invention is a size-determination of the PCR products generated. Size determination can be carried out according to any acceptable method, with gel electrophoresis being preferred. Methods for determining size of PCR products are described in Sambrook, supra and Ausubel, supra. Use of a control (identity known) sample or a sizing ladder is particularly helpful as well.

The present invention also includes kits useful for distinguishing between or among species of the same genus, comprising at least one set of genus-specific primers, said primers being capable of amplifying uniquely-sized fragments from at least a portion of an intergenic region of at least two species of said genus. The present kits preferably further comprise a gel material, such as, but not limited to, agarose or acrylamide.

Specifically, the present invention includes kits useful for distinguishing between or among Bartonella species, comprising at least one set of Bartonella genus-specific primers. The present kits preferably further comprise a gel material, such as, but not limited to, agarose or acrylamide.

Nucleic acid compounds are also provided by the present invention. Specifically, compositions of matter comprising forward and reverse Bartonella genus-specific primers as described herein are included in the present invention. Particular forward Bartonella genus-specific primers selected from the group consisting of: SEQ ID NO 5; SEQ ID NO 8; SEQ ID NO 9; SEQ ID NO 11; SEQ ID NO 14; SEQ ID NO 20; and SEQ ID NO 22 are included, with SEQ ID NO 5; SEQ ID NO 11; SEQ ID NO 14; SEQ ID NO 20; and SEQ ID NO 22 being preferred. More preferred is SEQ ID NO 20. Particular reverse Bartonella genus-specific primers selected from the group consisting of: SEQ ID NO 6; SEQ ID NO 7; SEQ ID NO 10; SEQ ID NO 12; SEQ ID NO 13; SEQ ID NO 15; SEQ ID NO 19; and SEQ ID NO 21 are also included, with SEQ ID NO 6; SEQ ID NO 10; SEQ ID NO 13; SEQ ID NO 19; and SEQ ID NO 21 being preferred. More preferred is SEQ ID NO 19.

The sequences described in the sequence listing can be shortened from the 5' end, provided that the resulting sequence does not result in loss of specificity when the shortened sequence is used as a primer. Those shortened primers are also useful as a part of a genus-specific primer set. For example, those primers wherein the 5' terminus is shortened by 1–10 bases are also within the scope of the present invention. Primers wherein the 5' terminus is shortened by 1–8 bases are preferred. Primers which are 14 bases in length and include at least one differentiating codon are most preferred. Any of these sequences can be used as primers in the methods described.

Also, with regard to the nucleic acid compounds herein provided, are isolated nucleic acid compounds comprising a 16S/23S intergenic sequence of *Bartonella clarridgeiae*, or a fragment thereof. Preferred nucleic acid compounds comprise SEQ ID NO 1, or a fragment thereof, and the antisense compound thereof, which is SEQ ID NO 2, or a fragment thereof. Moreover, vectors and cells comprising SEQ ID NO 1 and SEQ ID NO 2 or fragments thereof are also provided.

Isolated nucleic acid compounds comprising a 16S/23S intergenic sequence of *Bartonella vinsonii*, subspecies *berkhoffii*, or fragments thereof are also specifically provided. Preferred nucleic acid compounds comprise SEQ ID NO 3, or a fragment thereof, and the antisense compound thereof, which is SEQ ID NO 4, or a fragment thereof. Moreover, vectors and cells comprising SEQ ID NO 3 and SEQ ID NO 4 or fragments thereof are also provided.

A "fragment" as used herein, is a nucleic acid molecule which is subset of the referent compound, and which is at least 12 bases in length. Preferably the fragments herein are at least about 20, 30, 40 or 50 or 100 bases in length.

The vectors of the present invention can be any vector, including those derived from prokaryotes, eukaryotes or viruses. The vectors can be synthetic or hybrids of any of the materials described. The regulatory regions can be any promoter, terminator, enhancer or other regulatory signal or sequence. Cells of the present invention can be any cells, including bacterial, fungal and/or eukaryotic cells.

Included within the scope of the present invention, with particular regard to the nucleic acids above, are allelic variants, degenerate sequences and homologues. By "nucleic acid(s)" is meant any allelic variant, hybrids, and fragments thereof. "Allelic variant" is meant to refer to a sequence that occurs at essentially the same locus (or loci) as ther referent sequence (eg. SEQ ID NOs 1 through 4), but which, due to natural variations caused by, for example, mutation or recombination, has a similar but not identical sequence. Allelic variants are well known to those skilled in the art and would be expected to be found within intergenic sequences. The present invention also includes variants due to laboratory manipulation, such as, but not limited to, variants produced during polymerase chain reaction amplification or site directed mutagenesis. A nucleic acid sequence homologous to a nucleic acid herein is characterized by the ability to hybridize to the exemplified nucleic acid compounds (or allelic variants or degenerates thereof) under stringent conditions. Stringent hybridization conditions are described in Sambrook, et al., *Molecular Cloning: A Laboratory Manual*, at 9.47–9.51 (Cold Spring Harbor Laboratory Press, 1989).

In another embodiment of the present invention, there are provided methods to detect *Bartonella clarridgeiae* in a test sample, comprising: conducting polymerase chain reaction using starting materials which comprise genus- or species-specific primers constructed from SEQ ID NO 1 and/or SEQ ID NO 2, under conditions which allow production of an amplicon in the event that *Bartonella clarridgeiae* is present in the test sample; and detecting *Bartonella clarridgeiae* in the event that an amplicon is present.

Additionally, there are provided methods to detect *Bartonella vinsonii*, subspecies *berkhoffii* in a test sample, comprising: conducting polymerase chain reaction using starting materials which comprise genus- or species-specific primers constructed from SEQ ID NO 3 and/or SEQ ID NO 4, under conditions which allow production of an amplicon in the event that *Bartonella vinsonii*, subspecies *berkhoffii* is present in the test sample; and detecting *Bartonella vinsonii*, subspecies *berkhoffii* in the event that an amplicon is present.

Lastly, the present invention includes methods to design a set of primers capable of amplifying a uniquely-sized fragment from at least two species of a genus, comprising: identifying genomic fragments from at least two species of the same genus, said genomic fragments having differences in absolute size, and said genomic fragments being defined at least on the periphery by alignable conserved sequences; and identifying a forward and reverse sequence on the periphery which are common to each of the species for which primers are desired.

EXAMPLES

Example 1 Comparison of 16S-23S rRNA Intergenic Sequences of Bartonella Species

Figure 1:
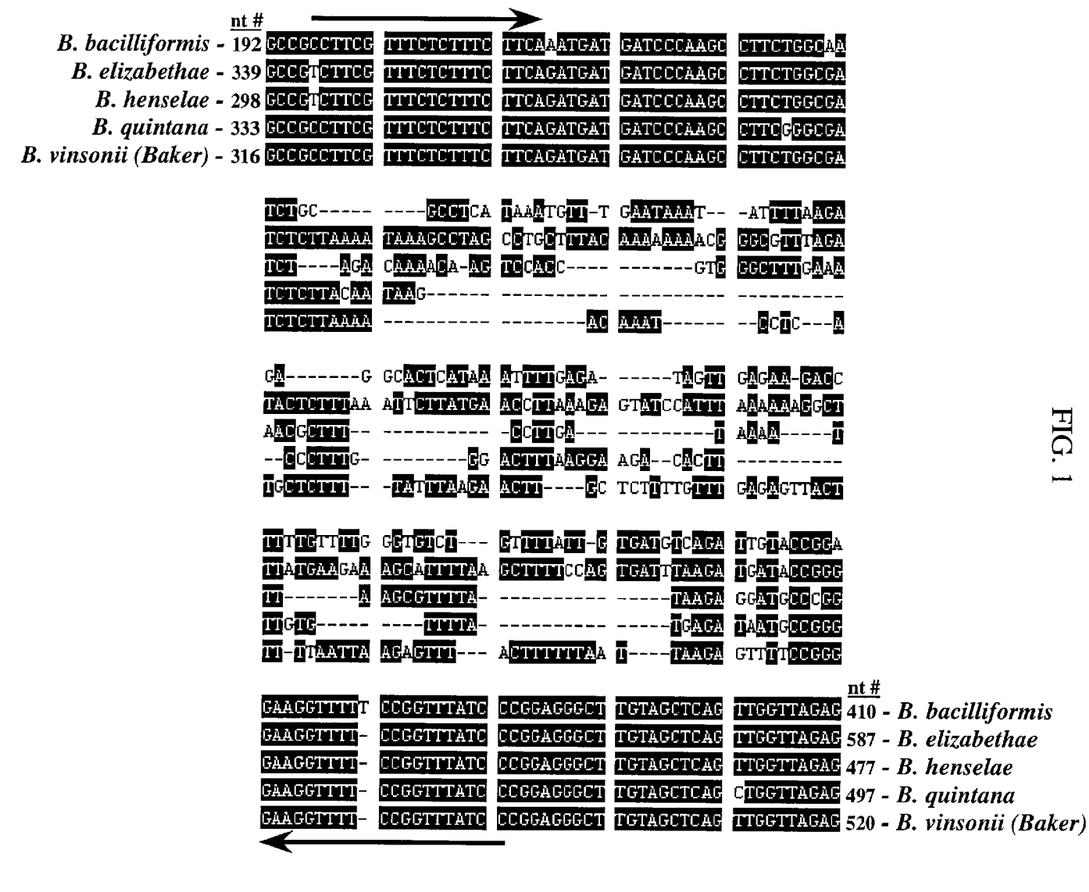
FIG. 1. Nucleotide sequence alignment of a portion of the 16S-23S rRNA intergenic region of B. bacilliformis (GenBank accession #L26364), B. elizabethae (#L35103), B. henselae (#L35101), B. quintana (#L35100), and B. vinsonii (baker strain) (#L35102). Corresponding GenBank nucleotide numbers are indicated at the beginning and end of the sequences. Arrows designate PCR primer positions.

The 16S-23S rRNA intergenic sequences for *B. bacilliformis* (Genbank accession #L26364, 25), *B. elizabethae* (#L35103, 30), *B. henselae* (#L35101, 30), *B. quintana* (#L35100, 30), and *B. vinsonii* (baker strain) (#L35102, 30)

were aligned using the DNA analysis computer program, DNAsis (Hitachi Software Engineering America Ltd., South San Francisco, Calif.). FIG. 1 illustrates alignment of approximately 200 nucleotides in the 5' region of the 16S-23S intergenic sequences. In this region, a non-conserved area is bordered by two areas of high homology. Individual Bartonella species differ in the non-conserved region primarily due to sequence insertions and/or deletions. The extent of variation suggested that PCR primers designed to amplify across the non-conserved region would generate amplified products of different sizes for each species of Bartonella. A PCR assay was designed to amplify the region shown in FIG. 1. Template DNA was obtained from *B. bacilliformis, B. clarridgeiae, B. elizabethae, B. henselae, B. quintana*, and *B. vinsonii* (subspecies *berkhoffii*). *B. koehlerae* was not available for analysis at the time this work was performed. Further analysis of *B. vinsonii* (baker strain) was not included because this Bartonella species has not been associated with disease in either humans or domestic animals. Template DNA was amplified using 5'-(C/T)CTTCGTTTCTCTTTCTTCA-3' (*B. henselae* nts 302–321, SEQ ID NO 14) and 5'-GGATAAACCGGAAAACCTTC-3' (*B. henselae* nts 448–429, SEQ ID NO 7)) as forward and reverse primers, respectively. The 16S-23S rRNA intergenic sequences predict that these primers should amplify products of 186 bp (*B. bacilliformis*), 216 bp (*B. elizabethae*), 147 bp (*B. henselae*), and 132 bp (*B. quintana*). A predicted product size could not be determined for *B. clarridgeiae* or *B. vinsonii* (subspecies *berkhoffii*) because sequence of the 16S-23S rRNA intergenic region for these Bartonella species has not been reported.

Example 2 Materials Used in PCR

Bacterial strains. *B. bacilliformis* (ATCC #35685), *B. clarridgeiae* (ATCC #51734 and #700095), *B. elizabethae* (ATCC #49927), *B. quintana* (ATCC #51694), *B. vinsonii* (subspecies *berkhoffii*) (ATCC #51672) were obtained from the American Type Culture Collection (Rockville, Md.). *B. henselae* isolates; Houston-1 (ATCC #49882), Oklahoma (ATCC #49793), Marseilles, MO-2, SA-1, CA-4, Tiger-2, and Lassiter were kindly provided by Russell Regnery, Viral and Rickettsial Diseases Branch, Centers for Disease Control and Prevention, Atlanta, Ga.

Clinical samples. Blood was obtained using aseptic procedures from the jugular vein of cats or dogs and placed in EDTA anti-coagulant tubes. Molecular characterization of *B. henselae, B. clarridgeiae*, and *B. vinsonii* (subspecies *berkhoffii*) isolates from these naturally-infected cats and dogs has been previously reported.

Example 3 DNA Extraction and PCR Amplification of the 16S-23S rRNA Intergenic Region DNA for PCR amplification was prepared from pure cultures of each bacterial strain using the QIAamp DNA Mini Kit (QIAGEN Inc., Valencia, Calif.) and from blood using the QIAamp DNA Blood Mini Kit. PCR amplifications were performed in 50 l containing 10 mM Tris, pH 8.3, 50 mM KCl, 3.5 mM MgCl$_2$, 200 M each dATP, dCTP, and dGTP, 400 µM dUTP, 1 M each primer, and 2.5 units Amplitaq Gold DNA polymerase (PE Applied Biosystems, Foster City, Calif.). Amplification buffer was optimized with dUTP for use with Uracil glycosylase to prevent PCR amplification product carryover. Optimum primer annealing temperatures were determined in a RoboCycler® Gradient Temperature Cycler (Stratagene, La Jolla, Calif.). Amplifications were performed in a GeneAmp PCR System 9700 thermal cycler (PE Applied Biosystems) using a time-release PCR protocol (13) as follows; 10 minute incubation at 20C followed by 2 minutes denaturation at 95° C. then 45 cycles of 1 minute denaturation at 95° C., 1 minute annealing at 60° C., and 30 second extension at 72C. PCR amplification products were identified by ethidium bromide fluorescence after electrophoresis in 3% agarose gels.

Example 4 Identifying Organisms Present

After amplification according to Example 3, PCR products were electrophoresed on a 3% agarose gel, stained with ethidium bromide and photographed. As shown in FIG. 2, the expected product size was amplified from *B. bacilliformis, B. elizabethae, B. henselae*, and *B. quintana* template DNA. The template DNA from *B. vinsonii* (subspecies *berkhoffii*) yielded a PCR product of approximately 235 bp rather than the 172 bp product predicted from the *B. vinsonii* (baker strain) sequence. PCR amplification of the *B. clarridgeiae* template DNA yielded no product using these primers.

Figure 4:
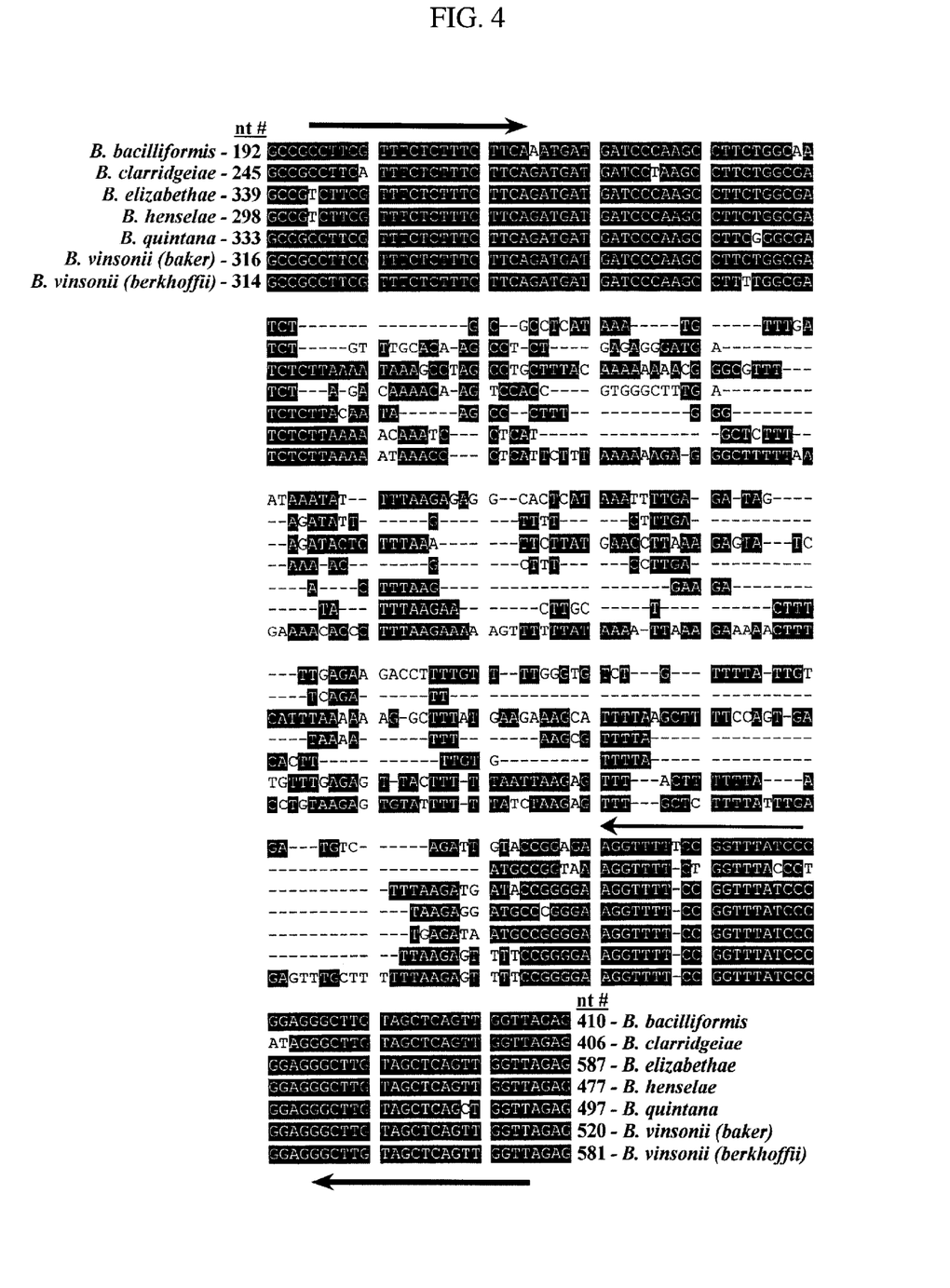
FIG. 4. Nucleotide sequence alignment of a portion of the 16S-23S rRNA intergenic region of B. bacilliformis (GenBank accession #L26364), B. clarridgeiae (GenBank accession #AF167989), B. elizabethae (#L35103), B. henselae (#L35101), B. quintana (#L35100), B. vinsonii (baker strain) (#L35102), and B. vinsonii (subspecies berkhoffii) (#AF167988). Corresponding GenBank nucleotide numbers are indicated at the beginning and end of the sequences. Arrows designate PCR primer positions. Non-conserved B. clarridgeiae nucleotide located at the 3' end of initial PCR primer used (see FIG. 1) denoted by an asterisk (*)
Figure 5:
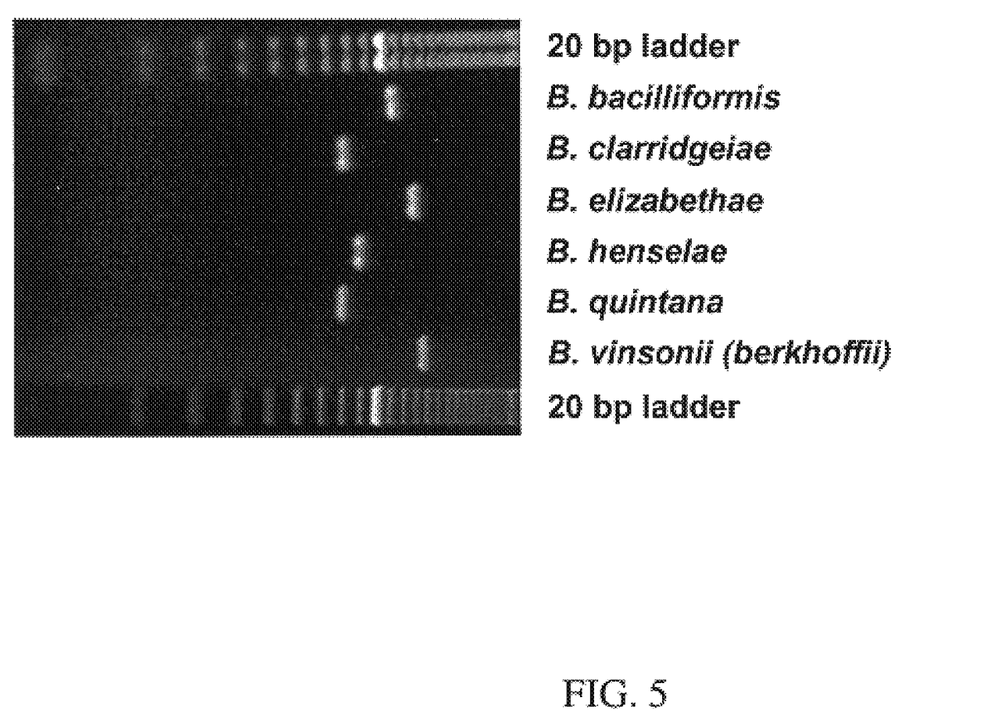
FIG. 5. PCR-based identification of Bartonella species. An ethidium bromide-stained agarose gel (3%) demonstrating amplified products from DNA template derived from Bartonella species. Bartonella bacilliformis, B. clarridgeiae, B. elizabethae, B. henselae, B. quintana, and B. vinsonii (subspecies berkhoffii) yielded expected products of 211, 154 bp, 241 bp, 172 bp, 157 bp, and 260 bp, respectively. First and last lanes contain 20 base pair ladder.

To detect and differentiate medically relevant Bartonella species, new primers complementary to 16S-23S rRNA intergenic region sequences shared by all of the Bartonella species were selected for PCR amplification (FIG. 4). Amplification of template DNA using 5'-(C/T)CTTCGTTTCTCTTTCTTCA-3' (*B. henselae* nts 302–321, SEQ ID NO 14) and 5'-AACCAACTGAGCTACAAGCC-3' (*B. henselae* nts 473–454, SEQ ID NO 19) as forward and reverse primers, respectively, resulted in amplified products corresponding to the predicted size, namely, 211 bp (*B. bacilliformis*), 154 bp (*B. clarridgeiae*), 241 bp (*B. elizabethae*), 172 bp (*B. henselae*), 157 bp (*B. quintana*), and 260 bp (*B. vinsonii* subspecies *berkhoffii*) (FIG. 5). Amplification of template DNA derived from the CA-4, MO-2, SA-1, Houston, Lassiter, Marseilles, Oklahoma, and Tiger-2 isolates of *B. henselae* yielded the same size amplification product, demonstrating conservation of this target region amongst different isolates of *B. henselae* (data not shown). Amplification of template DNA derived from *Clostridium perfringens, Enterobacter cloacae, Escherichia coli, Ehrlichia canis, Ehrlichia chaffeensis, Ehrlichia equi, Ehrlichia equi, Ehrlichia ewingii, Ehrlichia risticii, Fusobacterium necrophorum, Klebsiella pneumoniae, Salmonella choleraesuis*, and *Staphylococcus intermedius* did not result in product amplification (data not shown).

Example 5 Sequencing of the 16S-23S rRNA Intergenic Region for *B. clarridgeiae* and *B. vinsonii* (subspecies *berkhoffii*)

PCR amplification of the entire 16S-23S rRNA intergenic region was accomplished using primers described by Matar et al., 31(7) *J. Clin. Microb.* 1730 (1993) and Roux and Raoult, 33(6) *J. Clin. Microb.* 1573 (1995) PCR products amplified from the 16S-23S rRNA intergenic regions of *B. clarridgeiae* and *B. vinsonii* (subspecies *berkhoffii*) were sequenced using an ABI PRISM™ Model 377 with XL upgrade DNA Sequencer (PE Applied Biosystems) after product labeling using the PRISM™ Dye Terminator Cycle Sequencing Ready Reaction Kit (PE Applied Biosystems) following the manufacturer's protocol. Sequence alignments and phylogenetic comparisons were done with the DNA analysis computer program, DNAsis (Hitachi Software Engineering America Ltd., South San Francisco, Calif.).

Figure 6:
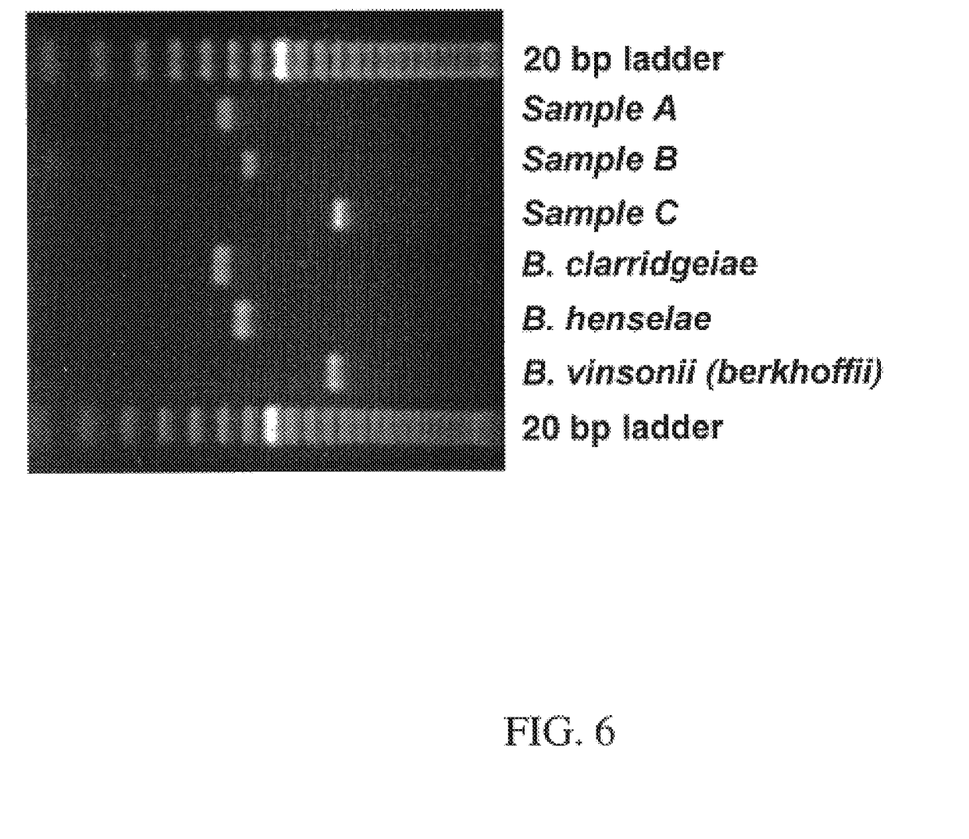
FIG. 6. PCR-based identification of Bartonella species from animals known to be infected with either B. clarridgeiae (Sample A), B. henselae (Sample B), or B. vinsonii (subspecies berkhoffii) (Sample C). DNA was extracted from 200 l of blood, eluted in a final volume of 2001 l, then 5 l of template DNA was used in each PCR amplification. After amplification, PCR products were electrophoresed on a 3% agarose gel and stained with ethidium bromide. Amplified control template DNA derived from isolated B. clarridgeiae, B. henselae, and B. vinsonii (subspecies berkhoffii) yielded expected products of 154 bp, 172 bp, and 260 bp, respectively. First and last lanes contain 20 base pair ladder.

To investigate the failure to amplify product from *B. clarridgeiae* and the discrepancy between the amplification product from *B. vinsonii* (subspecies *berkhoffii*) and the size predicted from the *B. vinsonii* (baker strain) sequence, the 16S-23S rRNA intergenic regions from *B. clarridgeiae* and *B. vinsonii* (subspecies *berkhoffii*) were sequenced (Genbank #'s AF167989 and AF167988, respectively). The 16S-23S rRNA intergenic sequence of *B. clarridgeiae* and *B. vinsonii* (subspecies *berkhoffii*) were compared with the reported sequences of *B. bacilliformis*, *B. elizabethae*, *B. henselae*, *B. quintana*, and *B. vinsonii* (baker strain) (FIG. 3). As expected, *B. vinsonii* (subspecies *berkhoffii*) is most closely related to *B. vinsonii* (baker strain). Alignment of the *B. vinsonii* (subspecies *berkhoffii*) 16S-23S rRNA intergenic region revealed 63 bp inserted in the target region relative to the *B. vinsonii* (baker strain) sequence (FIG. 4). Based on 16S-23S rRNA intergenic region sequences, *B. clarridgeiae* is most closely related to *B. bacilliformis* (FIG. 3). Analysis of the *B. clarridgeiae* 16S-23S rRNA intergenic region sequence revealed that the 3' nucleotide of the reverse PCR primer sequence is not conserved with other Bartonella species, thus explaining the inability to amplify a PCR product (FIG. 4). The 16S-23S rRNA intergenic sequences for *B. clarridgeiae* and *B. vinsonii* (subspecies *berkhoffii*), have been submitted to GenBank under accession no. AF167989 and AF167988, respectively Example 6. PCR Detection in Clinical Samples To evaluate the utility of this assay for detection of Bartonella species in clinical samples, DNA was prepared from blood of animals known to be infected with either *B. henselae*, *B. clarridgeiae*, or *B. vinsonii* (subspecies *berkhoffii*). Briefly, DNA was extracted from 200 l of blood using the QIAamp® Blood Kit (QIAGEN Inc., Santa Clarita, Calif.) and eluted in a final volume of 200 1 per the manufacturer's protocol. Samples (51 of template DNA) were amplified using the primers described above. After amplification, PCR products were electrophoresed on a 3% agarose gel, stained with ethidium bromide and photographed. As illustrated in FIG. 6, the single-step PCR assay is capable of detecting and differentiating infections with *B. henselae*, *B. clarridgeiae*, and *B. vinsonii* (subspecies *berkhoffii*) in clinical samples derived from naturally-infected animals.

Example 7. Sensitivity of PCR Versus Blood Culture for Detection of *B. henselae*

To determine the sensitivity of the single-step PCR assay relative to blood culture we purified template DNA from 200 l blood containing 10 to 100 CFU/ml of *B. henselae* derived from experimentally-infected cats. DNA was eluted in 200 l buffer and 5 l was used as template in the single-step PCR assay as described above. As shown in Table 1, the single-step PCR assay detected *B. henselae* in 100% of blood samples with 50–100 CFU/ml, 85% of blood samples with 30 CFU/ml, 75% of blood samples with 20 CFU/ml, and 75% of blood samples with 10 CFU/ml.

TABLE 1

Sensitivity of single-step PCR assay

| CFU's | Single-step PCR assay | |
|---|---|---|
| 50–100 | 12/12 | (100%) |
| 30 | 6/7 | (85%) |
| 20 | 3/4 | (75%) |
| 10 | 3/4 | (75%) |

What is claimed is:

1. A method to detect Bartonella species in a test sample, comprising:
   a) conducting polymerase chain reaction using starting materials which comprise a test sample and at least one set of Bartonella genus-specific primers to produce an amplicon, wherein said primers amplify at least a portion of a Bartonella 16S/23S intergenic region and do not amplify nucleic acid molecules from other genera;
   b) detecting an amplicon in the event a Bartonella species is present, and
   c) determining the size of said amplicon, wherein amplicon size is indicative of the Bartonella species present.

2. A method of claim 1, wherein step b) comprises gel electrophoresis.

3. A method of claim 1, wherein said set of Bartonella genus-specific primers includes a forward primer designed from the region spanning from base 300 through base 350, and a reverse primer designed from the region spanning from base 430 through base 530 of a *Bartonella henselae* 16S/23S intergenic region.

4. A method of claim 1, wherein said set of Bartonella genus-specific primers includes a forward primer selected from the group consisting of: SEQ ID NO 5; SEQ ID NO 9; SEQ ID NO 11; SEQ ID NO 14; SEQ ID NO 20; and SEQ ID NO 22.

5. A method of claim 1, wherein said set of Bartonella genus-specific primers includes a reverse primer selected from the group consisting of: SEQ ID NO 6; SEQ ID NO 7; SEQ ID NO 10; SEQ ID NO 12; SEQ ID NO 13; SEQ ID NO 19; and SEQ ID NO 21.

6. A method of claim 2, wherein the primers amplify a uniquely-sized amplicon from each of a Bartonella species selected from the group consisting of *B. henselae* and *B. clarridgeiae*.

7. A method to detect Bartonella-caused disease in a mammal, comprising:
   a) conducting polymerase chain reaction using starting materials which comprise a test, and at least one set of Bartonella genus-specific primers to produce an amplicon, wherein said primers amplify at least a portion of a Bartonella 16S/23S intergenic region and do not amplify nucleic acid molecules from other genera; and
   b) detecting a Bartonella organism which is causative of said disease in the test sample in the event an amplicon is present, wherein amplicon size is indicative of the Bartonella species present.

8. A method of claim 7, wherein the Bartonella-caused disease is bacilliary angiomatosis.

9. A method of claim 7, wherein the Bartonella-caused disease is cat scratch disease.

10. A method to detect cat-scratch disease in a mammal, comprising:
    a) conducting polymerase chain reaction using starting materials which comprise a test sample and at least one set of Bartonella genus-specific primers to produce an amplicon, wherein said primers amplify at least a portion of a Bartonella 16S/23S intergenic region and do not amplify nucleic acid molecules from other genera; and
    b) detecting a Bartonella organism which is causative of cat-scratch disease in the test sample in the event an amplicon is present, wherein the size of said amplicon is indicative of a species chosen from the group consisting of: *B. henselae*; and *B. clarridgeiae*.

11. A kit useful for distinguishing between or among Bartonella species, comprising at least one set of Bartonella genus-specific primers which amplify at least a portion of the 16S/23S intergenic region and do not amplify nucleic acid molecules from other genera.

12. A kit of claim 11, which further comprises gel material.

13. A composition of matter comprising a set of Bartonella genus-specific primers which amplify at least a portion of the 16S/23S intergenic region and do not amplify nucleic acid molecules from other genera.

14. A set of Bartonella genus-specific primers of claim 13, wherein said set of Bartonella genus-specific primers includes a forward primer selected from the group consisting of: SEQ ID NO 5; SEQ ID NO 9; SEQ ID NO 11; SEQ ID NO 14; SEQ ID NO 20; and SEQ ID NO 22.

15. A set of Bartonella genus-specific primers of claim 13, wherein said set of Bartonella genus-specific primers includes a reverse primer selected from the group consisting of: SEQ ID NO 6; SEQ ID NO 7; SEQ ID NO 10; SEQ ID NO 12; SEQ ID NO 13; SEQ ID NO 15; SEQ ID NO 19; and SEQ ID NO 21.

* * * * *

SEQUENCE LISTING

```
<160> NUMBER OF SEQ ID NOS: 22

<210> SEQ ID NO 1
<211> LENGTH: 1919
<212> TYPE: DNA
<213> ORGANISM: Bartonella clarridgeiae

<400> SEQUENCE: 1
acaaggtagc cgtaggggaa cctgtggctg gatcacctcc tttctaagga tgatcaagaa      60
tgggcctagg ccttttttga tctgattaga cattgacggt ttaaagtctt atttaaaccg     120
ttgacatatt ttaaacattc tatgaaccgt gggttttgaa tggaaactct gtcccctta     180 gtgatacaga gcataactgt tttttatcca tggttcattt gtttaaaaat ttataaaaag    240
actagccgcc ttcatttctc tttcttcaga tgatgatcct aagccttctg gcgatctgtt    300
tgcacaagcc tctgagaggg atgaagatat tgttttcttt gatcagatta tgccggtaaa    360
ggttttctgg tttaccctat agggcttgta gctcagttgg ttagagcgcg cgcttgataa    420
gcgtgaggtc ggaggttcaa gtcctcccag gcccaccagt tacacgatgc taaaagttgc    480
tatattggga gagttgataa tcccttacag gaaattattg ccctaataa aactttattt    540 tctaaaagca ttcagagctg acatagaata gagctgacat agaattgaga atctgacata    600
ggaattattg aaattgtttt ggaattattg aaattgtttt ctatcatttt aaaaggctaa    660
aatattctgt ctctattttt aaaatagcat caggtgtttt gtaagagtgt gaagttttta    720
agtgtgaggt tttttatatt ttagtgtgag gttttttataa gggtatgacg tgagagcgtt    780
```

```
ttgacctgtt ttaggggccg tagctcagct gggagagcac ctgctttgca agcagggggt      840
cgtcggttcg atcccgtccg gctccaccat aatttggttc atcattattg ttagaagaat      900
agttattgca agagattgag agatctcttt gcttgttcta ttgaaattgt gaagaagaag      960
gtatattcag acgttttttg cttgaactca ttcttatgaa agagattttt cttatgaaag     1020 agattttaa gaatggatag cttaaaaaga gaatggatg gcttaaaaag gtggcttaaa       1080
aaggatggct gtttttaaat gaaatagtt attttttacgc tcttttgacg attgttacaa     1140
cattatacga ttaaaacatt atacgataat gataataacg ataataaaaa gagctttcat     1200
taataaaaag agctttcatt aataataaag agctttcatt gaactttcat tgaagaagca     1260
ttttgagcaa aacagatgtg tcgcaaggaa gagctcaaat tccttgctta tgattggcaa     1320
cttaaccgtg ccattgaata tatctcgaga agttggtctt ttctgctgat attttttgttt  1380 taagtgccta ttgatgctag attattttta aaataatttt tgtattgatg attttgcacg     1440
gaataattga cgaatgaata ttggcaatga aatgatcaa gtgtcttaag ggcatttggt     1500
ggatgccttg gcatgcacag gcgaagaagg acgtgatacg ctgcgataag ctacggggag     1560
gtgcgaatac cctttgatcc gtagatttcc gaatggggca acccaccttta gattgctgga     1620 aaagttaagc tgctttagat taaagcggtt taattttcta gcaatcacta attaaggtat     1680
ctgcatctga ataaaatagg gtgtaagaag cgaacgcagg gaactgaaac atctaagtac     1740
ctgtaggaaa ggacatcaat agagactccg ttagtagtgg cgagcgaacg cggaccaggc     1800
cagtggctta agttaagaaa agtagaatcg attggaaagt cgaaccaaag agggtgatag     1860
tcccgtatac gtagatctga tttaagtcct tgagtaaggc gggacacgtg aaatcctgt     1919
```

<210> SEQ ID NO 2
<211> LENGTH: 1919
<212> TYPE: DNA
<213> ORGANISM: Bartonella clarridgeiae

<400> SEQUENCE: 2

```
acaggatttc acgtgtcccg ccttactcaa ggacttaaat cagatctacg tatacgggac       60
tatcaccctc tttggttcga ctttccaatc gattctactt ttcttaactt aagccactgg      120
cctggtccgc gttcgctcgc cactactaac ggagtctcta ttgatgtcct ttcctacagg      180
tacttagatg tttcagttcc ctgcgttcgc ttcttacacc ctatttttatt cagatgcaga     240 taccttaatt agtgattgct agaaaattaa accgctttaa tctaaagcag cttaactttt     300
ccagcaatct aaggtgggtt gccccattcg gaaatctacg gatcaaaggg tattcgcacc     360
tccccgtagc ttatcgcagc gtatcacgtc cttcttcgcc tgtgcatgcc aaggcatcca     420
ccaaatgccc ttaagacact tgatcattct cattgccaat attcattcgt caattattcc     480
gtgcaaaatc atcaatacaa aattatttt aaaaataatc tagcatcaat aggcacttaa     540
aacaaaaata tcagcagaaa agaccaactt ctcgagatat attcaatggc acggttaagt     600
tgccaatcat aagcaaggaa tttgagctct tccttgcgac acatctgttt tgctcaaaat     660
gcttcttcaa tgaaagttca atgaaagctc tttattatta tgaaagctc ttttttattaa    720 tgaaagctct ttttattatc gttattatca ttatcgtata atgttttaat cgtataatgt     780
tgtaacaatc gtcaaagag cgtaaaaata actattttca tttaaaaaca gccatccttt     840
ttaagccacc ttttaagcc atccattctt ctttttaagc tatccattct taaaaatctc     900
tttcataaga aaaatctctt tcataagaat gagttcaagc aaaaaacgtc tgaatatacc     960
```

-continued

| | |
|---|---|
| ttcttcttca caatttcaat agaacaagca aagagatctc tcaatctctt gcaataacta | 1020 |
| ttcttctaac aataatgatg aaccaaatta tggtggagcc ggacgggatc gaaccgacga | 1080 |
| cccctgctt gcaaagcagg tgctctccca gctgagctac ggcccctaaa acaggtcaaa | 1140 |
| acgctctcac gtcataccct tataaaaacc tcacactaaa atataaaaaa cctcacactt | 1200 |
| aaaaacttca cactcttaca aaacacctga tgctatttta aaaatagaga cagaatattt | 1260 |
| tagcctttta aaatgataga aaacaatttc aataattcca aaacaatttc aataattcct | 1320 |
| atgtcagatt ctcaattcta tgtcagctct attctatgtc agctctgaat gcttttagaa | 1380 |
| aataaagttt tattaagggc aataatttcc tgtaagggat tatcaactct cccaatatag | 1440 |
| caacttttag catcgtgtaa ctggtgggcc tgggaggact tgaacctccg acctcacgct | 1500 |
| tatcaagcgc gcgctctaac caactgagct acaagcccta tagggtaaac cagaaaacct | 1560 |
| ttaccggcat aatctgatca agaaaacaa tatcttcatc cctctcagag gcttgtgcaa | 1620 |
| acagatcgcc agaaggctta ggatcatcat ctgaagaaag agaaatgaag gcggctagtc | 1680 |
| tttttataaa ttttttaaaca aatgaaccat ggataaaaaa cagttatgct ctgtatcact | 1740 |
| aaaggggaca gagtttccat tcaaaaccca cggttcatag aatgtttaaa atatgtcaac | 1800 |
| ggtttaaata agacttttaaa ccgtcaatgt ctaatcagat caaaaaaggc ctaggcccat | 1860 |
| tcttgatcat ccttagaaag gaggtgatcc agccacaggt tcccctacgg ctaccttgt | 1919 |

<210> SEQ ID NO 3
<211> LENGTH: 1883
<212> TYPE: DNA
<213> ORGANISM: Bartonella vinsonii

<400> SEQUENCE: 3

| | |
|---|---|
| gggcaggcaa ccacggtagg gtcagcgact ggggtgaagt cgtaacaagg tagccgtagg | 60 |
| ggaacctgtg gctggatcac ctcctttcta aggatgatca aaaattggga aatcctctct | 120 |
| ttttgatctc atttagacac gggtttaaac ttattcgttt aaaccgtgca tatgacacta | 180 |
| acgctcaact ctataccctc tctcaaaaga gaacctctta acaagaggc cctaatctct | 240 |
| tgaggcccct acctccgatg agatggtgtt catgagggct tagtgatcat gtgtaaaaat | 300 |
| aacaggcagg cttgccgcct tcgtttctct ttcttcagat gatgatccca agccttttgg | 360 |
| cgatctctta aaataaacc ctcattcttt aaaaagagg gcttttaag aaaacacccct | 420 |
| ttaagaaaaa gttttttata aaattaaaga aaaactttcc tgtaagagtg tattttttat | 480 |
| ctaagagttt gctctttttat ttgagagttt gcttttttaa gagttttccg gggaaggttt | 540 |
| tccggtttat cccggagggc ttgtagctca gttggttaga gcgcgcgctt gataagcgtg | 600 |
| aggtcggagg ttcaagtcct cccaggccca ccaatttaga attaccaatt ggaattgctt | 660 |
| aacccactgt tgagaaactc cctcctttat gagagaaatc tctaaaaaca agagaaagct | 720 |
| cttgagagcc tcaaatgata gatttcaaat tctcaataag atttaaaccc atcagatcta | 780 |
| aatcaataag gttaaaagt gttggtaaaa tgttcataat atattttata aaatattga | 840 |
| gaattatgga gatattaaga gattttttcgg acactattga taaatcttgg taagaaaatt | 900 |
| gataaaaatc ggtttagggg ttagcgcttt cgtttagggg ccgtagctca gctgggagag | 960 |
| cacctgcttt gcaagcaggg ggtcgtcggt tcgatcccgt ccggctccac cactttaggt | 1020 |
| catcatcatt gttatgagaa ccgtctttag tgatgaggct ttataacctt tcgctcgttc | 1080 |
| tattgaaatt gtgaagagaa gatatattca gacattgttc ctttggggat gtttgttttg | 1140 |
| aaagaagcaa gcttttttgtg aagaaaaatg cttgtggtca ggaaaaacgc ttcgttgaag | 1200 |

-continued

```
aagaaacatc aaaagggtct ctcaaagaaa cccaagaaag aaaccaagaa acattgtgtc      1260
gcaagggaat gctcaaagcc cttgcttatg attggaagct taaccgcgcc attgaatata      1320
tctcgagaag ctggtctttt ctgctgatat tttgtttgtt ttgcccttt tgttttgcac       1380 aaggcaaaaa aagagacaaa cgctgaatga atattggcaa tgagaacgat caagtgtctt      1440
aagggcattt ggtggatgcc ttggcatgca caggcgatga aggacgtgat acgctgcgat      1500
aagctacggg gaggtgcgaa tacccttga tccgtagatc tccgaatggg caacccacc        1560 tttgatggct agaaaaatta agctgttttt acaaaaagac agtttagttt tctagtcgtc      1620
agataaaggt atctacacct gaataaaata gggtgtaaga agcaaacgca gggaactgaa      1680
acatctaagt acctgtagga aaggacatca aacgagactc cgttagtagt ggcgagcgaa      1740
cgcggaccag gccagtggct taaattaaga aaagtagaat cgactggaaa gtcgaaccaa      1800
agtgggtgat agtcccgtat acgtaaatct gatttaagtc ctagagtagg gcgggacacg      1860
tgaaatcctg tctgaatatg ggt                                              1883
```

<210> SEQ ID NO 4
<211> LENGTH: 1883
<212> TYPE: DNA
<213> ORGANISM: Bartonella vinsonii

<400> SEQUENCE: 4

```
acccatattc agacaggatt tcacgtgtcc cgccctactc taggacttaa atcagattta     60
cgtatacggg actatcaccc actttggttc gactttccag tcgattctac ttttcttaat    120
ttaagccact ggcctggtcc gcgttcgctc gccactacta acggagtctc gtttgatgtc    180
ctttcctaca ggtacttaga tgtttcagtt ccctgcgttt gcttcttaca ccctatttta    240
ttcaggtgta gatacccttta tctgacgact agaaaactaa actgtctttt tgtaaaaaca    300
gcttaatttt tctagccatc aaaggtgggt tgccccattc ggagatctac ggatcaaagg    360
gtattcgcac ctccccgtag cttatcgcag cgtatcacgt ccttcatcgc ctgtgcatgc    420
caaggcatcc accaaatgcc cttaagacac ttgatcgttc tcattgccaa tattcattca    480
gcgtttgtct cttttttgc cttgtgcaaa acaaaaaggg caaaacaaac aaaatatcag     540
cagaaaagac cagcttctcg agatatattc aatggcgcgg ttaagcttcc aatcataagc    600
aagggctttg agcattccct tgcgacacaa tgtttcttgg tttctttctt gggtttcttt    660
gagagaccct tttgatgttt cttcttcaac gaagcgtttt tcctgaccac aagcattttt    720
cttcacaaaa agcttgcttc tttcaaaaca aacatcccca aaggaacaat gtctgaatat    780
atcttctctt cacaatttca atagaacgag cgaaaggtta taaagcctca tcactaaaga    840
cggttctcat aacaatgatg atgacctaaa gtggtggagc cggacgggat cgaaccgacg    900
acccccctgct tgcaaagcag gtgctctccc agctgagcta cggcccctaa acgaaagcgc    960
taacccctaa accgattttt atcaattttc ttaccaagat ttatcaatag tgtccgaaaa   1020
atctcttaat atctccataa ttctcaatat ttttataaaa tatattatga acattttacc   1080
aacactttta aaccttattg atttagatct gatgggttta aatcttattg agaatttgaa   1140
atctatcatt tgaggctctc aagagctttc tcttgttttt agagatttct ctcataaagg   1200
agggagtttc tcaacagtgg gttaagcaat tccaattggt aattctaaat tggtgggcct   1260
gggaggactt gaacctccga cctcacgctt atcaagcgcg cgctctaacc aactgagcta   1320
caagccctcc gggataaacc ggaaaacctt ccccggaaaa ctcttaaaaa agcaaactct   1380
```

-continued

```
caaataaaag agcaaactct tagataaaaa atacactctt acaggaaagt ttttctttaa    1440 tttttataaaa aacttttttct taaagggtgt tttcttaaaa agccctcttt tttaaagaat   1500
gagggtttat ttttaagaga tcgccaaaag gcttgggatc atcatctgaa gaaagagaaa    1560
cgaaggcggc aagcctgcct gttattttta cacatgatca ctaagccctc atgaacacca    1620
tctcatcgga ggtaggggcc tcaagagatt agggcctctt tgttaagagg ttctcttttg    1680
agagagggta tagagttgag cgttagtgtc atatgcacgg tttaaacgaa taagtttaaa    1740
cccgtgtcta aatgagatca aaagagagg atttcccaat ttttgatcat ccttagaaag    1800
gaggtgatcc agccacaggt tcccctacgg ctaccttgtt acgacttcac cccagtcgct    1860
gaccctaccg tggttgcctg ccc                                            1883
```

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer A7518H09

<400> SEQUENCE: 5
gctggatcac ctcctttcta                                                20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer A7518H10

<400> SEQUENCE: 6
tccgacctca cgcttatcaa                                                20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer A7518H12

<400> SEQUENCE: 7
ggataaaccg gaaaaccttc                                                20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer A7620C06

<400> SEQUENCE: 8
gatgatgatc ccaagccttc                                                20

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer A8410C08

-continued

```
<400> SEQUENCE: 9
cgtaggggaa cctgtggc                                                    18

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence:  Synthetic
      Primer A8410C09

<400> SEQUENCE: 10
aacctccgac ctcacgct                                                    18

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence:  Synthetic
      Primer A8410C10

<400> SEQUENCE: 11
ctttcttcag atgatgat                                                    18

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence:  Synthetic
      Primer A8450A02

<400> SEQUENCE: 12
ataaaccgga aaacctt                                                     17

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence:  Synthetic
      Primer A8410C11

<400> SEQUENCE: 13
taaccaactg agctacaa                                                    18

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence:  Synthetic
      Primer A7518H11

<400> SEQUENCE: 14
tcttcgtttc tctttcttca                                                  20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence:  Synthetic
      Primer A8120F10

<400> SEQUENCE: 15
```
tactggttca ctatcggtca                                           20

<210> SEQ ID NO 16
<211> LENGTH: 15
<212> TYPE: DNA
<213> ORGANISM: Artificial Sequence
<220> FEATURE:
<223> OTHER INFORMATION: Description of Artificial Sequence: Synthetic
      Primer A8120F11

<400> SEQUENCE: 16
gccaaggcat ccacc                                                15

<210> SEQ ID NO 17
<211> LENGTH: 16
<212> TYPE: DNA
<213> ORGANISM: Artificial Sequence
<220> FEATURE:
<223> OTHER INFORMATION: Description of Artificial Sequence: Synthetic
      Primer A8744A03

<400> SEQUENCE: 17
aagtcgtaac aaggta                                               16

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer A8744A04

<400> SEQUENCE: 18
agaggcaggc aaccacggta                                           20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer Z5610H12

<400> SEQUENCE: 19
aaccaactga gctacaagcc                                           20

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 20
ctctttcttc agatgatgat cc                                        22

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 21

-continued

```
taaccaactg agctacaagc                                              20

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 22
tttctctttc ttcagatgat gatcc                                        25
```